United States Patent
Murakawa et al.

(10) Patent No.: US 7,994,183 B2
(45) Date of Patent: Aug. 9, 2011

(54) SOLID PREPARATION COMPRISING 2-[[6-[(3R)-3-AMINO-1-PIPERIDINYL]-3,4-DIHYDRO-3-METHYL-2,4-DIOXO-1(2H)-PYRIMIDINYL]METHYL]-4-FLUOROBENZONITRILE

(75) Inventors: Yusuke Murakawa, Osaka (JP); Miyuki Hohokabe, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 12/450,118

(22) PCT Filed: Mar. 12, 2008

(86) PCT No.: PCT/JP2008/055016
§ 371 (c)(1),
(2), (4) Date: Sep. 11, 2009

(87) PCT Pub. No.: WO2008/114800
PCT Pub. Date: Sep. 25, 2008

(65) Prior Publication Data
US 2010/0105710 A1     Apr. 29, 2010

(30) Foreign Application Priority Data
Mar. 13, 2007 (JP) .................. 2007-064245

(51) Int. Cl.
*A01N 43/54* (2006.01)
*A61K 31/505* (2006.01)
*C07D 239/02* (2006.01)
(52) U.S. Cl. ........................ 514/274; 544/309
(58) Field of Classification Search .............. 514/274
See application file for complete search history.

(56) References Cited

U.S. PATENT DOCUMENTS

| 5,009,897 | A | * | 4/1991 | Brinker et al. ............... 424/469 |
| 5,855,914 | A | * | 1/1999 | Koyama et al. ............... 424/494 |
| 2005/0215573 | A1 | * | 9/2005 | Schilling et al. ............ 514/266.2 |
| 2005/0261271 | A1 | | 11/2005 | Feng et al. |
| 2007/0060530 | A1 | | 3/2007 | Christopher et al. |
| 2008/0275072 | A1 | | 11/2008 | Ogawa |
| 2008/0287476 | A1 | | 11/2008 | Christopher et al. |

FOREIGN PATENT DOCUMENTS

| WO | WO 2005/067976 A2 | 7/2005 |
| WO | WO 2007/033350 A1 | 3/2007 |
| WO | WO 2008/067465 A1 | 6/2008 |
| WO | WO 2008/093878 A1 | 8/2008 |
| WO | WO 2009/022009 A1 | 2/2009 |

OTHER PUBLICATIONS

Communication issued Feb. 1, 2010, in corresponding EP 08 722 406.9, 6 pages.
International Search Report dated Oct. 17, 2008 in prior PCT/JP2008/055016, 4 pages.

\* cited by examiner

*Primary Examiner* — Sreeni Padmanabhan
*Assistant Examiner* — Layla Soroush
(74) *Attorney, Agent, or Firm* — Foley & Lardner LLP

(57) ABSTRACT

The present invention provides a solid preparation containing 2[[6-[(3R)-3-amino-1-piperidinyl]-3,4-dihydro-3-methyl-2,4-dioxo-1(2H)-pyrimidinyl]methyl]-4-fluorobenzonitrile (compound (A)) or a salt thereof as a pharmaceutically active ingredient. Specifically, the present invention provides a solid preparation containing a granule composed of compound (A) or a salt thereof and an additive (excluding microcrystalline cellulose) and a tablet containing (a) a granule containing compound (A) or a salt thereof and microcrystalline cellulose, and (b) a tableting aid containing magnesium stearate and microcrystalline cellulose.

7 Claims, No Drawings

SOLID PREPARATION COMPRISING 2-[[6-[(3R)-3-AMINO-1-PIPERIDINYL]-3,4-DIHYDRO-3-METHYL-2,4-DIOXO-1(2H)-PYRIMIDINYL]METHYL]-4-FLUOROBENZONITRILE

TECHNICAL FIELD OF THE INVENTION

The present invention relates to a solid preparation comprising 2-[[6-[(3R)-3-amino-1-piperidinyl]-3,4-dihydro-3-methyl-2,4-dioxo-1(2H)-pyrimidinyl]methyl]-4-fluorobenzonitrile (hereinafter sometimes to be abbreviated as compound (A)) or a salt thereof.

BACKGROUND OF THE INVENTION

Compound (A) or a salt thereof has been reported to be an inhibitor of dipeptidyl peptidase (DPP-IV), which is an enzyme that degrades glucagon-like peptide-1 (GLP-1), a hormone enhancing insulin secretion (US-A-2005/0261271).

DISCLOSURE OF THE INVENTION

The present invention aims at providing a solid preparation containing compound (A) or a salt thereof as a pharmaceutically active ingredient (to be also referred to as "solid preparation of compound (A)").

The present inventors have conducted intensive studies in an attempt to solve the above-mentioned problems and first found that microcrystalline cellulose, an additive conventionally used in the field of pharmaceutical preparation, can influence the stability of compound (A) in a preparation, and also suppresses tableting trouble that may occur during the process of preparation making due to the properties of compound (A), and conducted further studies to complete the present invention.

Accordingly, the present invention relates to

[1] a granule composed of compound (A) or a salt thereof and an additive, wherein the additive does not comprise microcrystalline cellulose,
[2] a solid preparation comprising the granule of the above-mentioned [1],
[3] the solid preparation of the above-mentioned [2], comprising 1-25 wt % of compound (A) relative to the solid preparation,
[4] a tablet comprising the following (a) and (b):
(a) a granule comprising compound (A) or a salt thereof and microcrystalline cellulose; and
(b) a tableting aid comprising magnesium stearate and microcrystalline cellulose,
[5] the tablet of the above-mentioned [4], wherein the content of the microcrystalline cellulose of the aforementioned (a) is 5-40 wt % and the content of the microcrystalline cellulose of the aforementioned (b) is 2-20 wt %, both relative to the tablet,
[6] the tablet of the above-mentioned [4], wherein the compound (A) is contained in a proportion of more than 25 wt % to not more than 40 wt % relative to the tablet,
[7] a method of producing a tablet, which comprises mixing (a) a granule comprising compound (A) or a salt thereof and microcrystalline cellulose, and (b) a tableting aid comprising magnesium stearate and microcrystalline cellulose, and then punching the mixture,
[8] the production method of the above-mentioned [7], wherein the content of the microcrystalline cellulose of the aforementioned (a) is 5-40 wt % and the content of the microcrystalline cellulose of the aforementioned (b) is 2-20 wt %, both relative to the tablet,
[9] the production method of the above-mentioned [7], wherein the compound (A) is contained in a proportion of more than 25 wt % to not more than 40 wt % relative to the tablet,
[10] a tablet obtained by the method of the above-mentioned [7];
and the like.

In the following, the above-mentioned granule, solid preparation and tablet are sometimes to be collectively abbreviated as "the preparation of the present invention".

Effect of the Invention

According to the present invention, a solid preparation of compound (A) superior in the formability, dissolution property and storage stability of compound (A) and the like can be provided.

DETAILED DESCRIPTION OF THE INVENTION

The present invention is explained in detail in the following.

Examples of the salt of compound (A) include a pharmacologically acceptable salt, such as a salt with inorganic acid, a salt with organic acid, a salt with basic or acidic amino acid and the like.

Preferable examples of the salt with inorganic acid include salts with hydrochloric acid, hydrobromic acid, nitric acid, sulfuric acid, phosphoric acid and the like.

Preferable examples of the salt with organic acid include salts with benzoic acid, formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like, and preferable examples of the salt with acidic amino acid include salts with aspartic acid, glutamic acid and the like.

Preferable examples of the salt of compound (A) include salts with trifluoroacetic acid, succinic acid, hydrochloric acid and the like. Of these, succinate of compound (A) is preferable.

Compound (A) may be a solvate (e.g., hydrate) or non-solvate.

Compound (A) may be labeled with an isotope (e.g., $^3$H, $^{14}$C, $^{35}$S, $^{125}$I) and the like.

Furthermore, a deuterium-converted compound wherein $^1$H has been converted to $^2$H(D) is also encompassed in the compound (A).

In the present specification, the "tableting trouble" means unpreferable phenomena experienced during tableting, such as sticking (attachment of powder to punch), binding (increased friction between tablet and die), capping (cap-like breakage of tablet), laminating (layer-like breakage of tablet) and the like.

In the present specification, the "granule" means granules having almost the same size and shape, which are obtained by granulating a starting material such as powder, bulk, solution, molten liquid and the like by a wet granulation method, a dry granulation method, a heating granulation method and the like.

The granules (the below-mentioned granule (A) and granule (B)) to be used in the present invention have a particle size of generally not less than 1000 μm for not more than 20%, not more than 150 μm for not more than 65% (with 16M sieves, on (remaining on sieves): not more than 20%; with 100M sieves, pass (pass through sieves): not more than 65%), preferably not less than 1000 μm for not more than 5%, not more than 150 μm for not more than 40% (with 16M sieves, on: not more than 5%; with 100 M sieves, pass: not more than 40%). Here, the particle size is, for example, a value obtained by measuring the weight of the granules remaining on the standard sieves after passage therethrough.

The granules may have different sizes and shapes during the process of preparation making (e.g., tableting step) to obtain the preparation of the present invention.

In one aspect, the present invention relates to granules (sometimes to be abbreviated as "granule (A)" in the present specification) composed of compound (A) or a salt thereof and an additive (excluding microcrystalline cellulose).

As compared to granules containing microcrystalline cellulose as an additive, granule (A) does not cause decomposition of compound (A) or a salt thereof easily. Using granule (A), therefore, a solid preparation of compound (A) superior in storage stability and the like can be provided.

In general, the size and weight of a solid preparation are limited to facilitate handling and administration. When the content of compound (A) in the preparation is reduced, the reduced amount needs to be compensated for by increasing the content of various additives. In other words, when the content of compound (A) in the preparation decreases, the content of additives increases inversely. As a result, compound (A) is exposed to an increased amount of additives in the preparation. When a solid preparation having a low content of compound (A) in the preparation (e.g., as compound (A) (i.e., as free form), not more than 25 wt %) is to be produced, therefore, use of granule (A) in an attempt to suppress decomposition of compound (A) due to the additive is advantageous.

This aspect also relates to a solid preparation containing granule (A) (sometimes to be abbreviated as "solid preparation (A)" in the present specification).

Granule (A) per se may be used as a preparation (such embodiment is also encompassed in the solid preparation (A) of the present invention).

Granule (A) and solid preparation (A) are explained in more detail in the following.

The content of compound (A) or a salt thereof in solid preparation (A) of the present invention is generally 0.1-50 wt %, preferably 1-25 wt %, more preferably 1-20 wt %, as compound (A) (free form).

As additives in granule (A), additives conventionally used in the preparation field, other than microcrystalline cellulose, are used. Examples of the additive include excipient, disintegrant, binder, lubricant, colorant, pH adjusting agent, surfactant, stabilizer, acidulant, flavor, glidant, coating base, coating additive and the like (unless particularly indicated, from the aspect of granule (A), microcrystalline cellulose is not included in these additives). Unless otherwise specified, these additives are used in an amount conventionally used in the preparation field.

Preferable examples of the excipient include mannitol; starches such as corn starch, potato starch, wheat starch, rice starch, partly pregelatinized starch, pregelatinized starch, porous starch and the like; anhydrous calcium phosphate; precipitated calcium carbonate; calcium silicate and the like.

As an excipient for granule (A), mannitol is preferable.

The content of the excipient contained in granule (A) in solid preparation (A) of the present invention is preferably 10-99.9 wt %, more preferably 35-80 wt %.

Preferable examples of the disintegrant include corn starch, carboxymethylcellulose, calcium carboxymethylcellulose, sodium carboxymethyl starch, croscarmellose sodium (e.g., Ac-Di-Sol), crospovidone, low-substituted hydroxypropylcellulose (L-HPC), hydroxypropylstarch and the like.

As a disintegrant for granule (A), corn starch is preferable.

The content of the disintegrant contained in granule (A) in solid preparation (A) of the present invention is preferably 1-50 wt %, more preferably 8-40 wt %.

Preferable examples of the binder include hydroxypropylcellulose [e.g., grade: L, SL, SL-T, SSL (trade name); Nippon Soda Co., Ltd.], hydroxypropylmethylcellulose [e.g., hypromellose 2910, TC-5 (grade: MW, E, EW, R, RW) (trade name); Shin-Etsu Chemical Co., Ltd.], povidone (polyvinylpyrrolidone), copovidone and the like.

The binder in granule (A) is preferably hydroxypropylmethylcellulose, povidone or copovidone, more preferably hydroxypropylmethylcellulose, in order to reduce an influence on the stability of compound (A).

The content of the binder contained in granule (A) in solid preparation (A) of the present invention is preferably 1-30 wt %, more preferably 2-20 wt %.

Preferable examples of the lubricant include magnesium stearate, calcium stearate, talc, sucrose esters of fatty acids, sodium stearyl fumarate and the like.

Preferable examples of the colorant include food colors such as Food Color Yellow No. 5, Food Color Red No. 2, Food Color Blue No. 2 and the like, food lake colors, red ferric oxide, yellow ferric oxide and the like.

Preferable examples of the pH adjusting agent include citric acid or a salt thereof, phosphoric acid or a salt thereof, carbonic acid or a salt thereof, tartaric acid or a salt thereof, fumaric acid or a salt thereof, acetic acid or a salt thereof, amino acid or a salt thereof and the like.

Preferable examples of the surfactant include sodium lauryl sulfate, polysorbate 80, polyoxyethylene(160)polyoxypropylene(30)glycol and the like.

Preferable examples of the stabilizer include succinic acid, tartaric acid, citric acid, lactic acid, fumaric acid, malic acid, ascorbic acid, acetic acid, acidic amino acid (e.g., glutamic acid, aspartic acid), inorganic salts of these acids (e.g., alkali metal salt, alkaline earth metal salt), salts with inorganic bases (e.g., ammonium) of these acids, salts with organic bases (e.g., meglumine) of these acids, salts with basic amino acid (e.g., arginine, lysine, ornithine), hydrates thereof, solvates thereof and the like.

In an attempt to improve the stability of compound (A), the above-mentioned stabilizer may be added to granule (A).

As a stabilizer for granule (A), succinic acid is preferable.

The content of the stabilizer contained in granule (A) in solid preparation (A) of the present invention is preferably 1-35 wt %, more preferably 3-10 wt %.

Preferable examples of the acidulant include ascorbic acid, citric acid, tartaric acid, malic acid and the like.

Preferable examples of the flavor include menthol, peppermint oil, lemon oil, vanillin and the like.

Preferable examples of the glidant include light anhydrous silicic acid, hydrated silicon dioxide and the like.

Preferable examples of the coating base include sugar coating base, aqueous film coating base, enteric film coating base, sustained-release film coating base and the like.

As the sugar coating base, for example, sucrose can be mentioned, and one or more kinds selected from talc, precipitated calcium carbonate, gelatin, gum arabic, pullulan, carnauba wax and the like may be used in combination.

Examples of the aqueous film coating base include cellulose polymers such as hydroxypropylcellulose [e.g., grade: L, SL, SL-T, SSL (trade name); Nippon Soda Co., Ltd.], hydroxypropylmethylcellulose [e.g., hypromellose 2910, TC-5

(grade: MW, E, EW, R, RW) (trade name); Shin-Etsu Chemical Co., Ltd.], hydroxyethylcellulose, methylhydroxyethylcellulose and the like; synthesis polymers such as polyvinyl acetaldiethylaminoacetate, aminoalkylmethacrylate copolymer E [Eudragit E (trade name)], polyvinylpyrrolidone and the like; polysaccharides such as pullulan and the like; and the like.

Examples of the enteric film coating base include cellulose polymers such as hydroxypropylmethylcellulose phthalate, hydroxypropylmethylcellulose acetatesuccinate, carboxymethylethylcellulose, cellulose acetate phthalate and the like; acrylic acid polymers such as methacrylic acid copolymer L [Eudragit L (trade name)], methacrylic acid copolymer LD [Eudragit L-30D55 (trade name)], methacrylic acid copolymer S [Eudragit S (trade name)] and the like; naturally occurring substances such as shellac and the like; and the like.

Examples of the sustained-release film coating base include cellulose polymers such as ethylcellulose and the like; acrylic acid polymers such as aminoalkyl methacrylate copolymer RS [Eudragit RS (trade name)], ethyl acrylate-.methacrylic acid methyl copolymer suspension [Eudragit NE (trade name)] and the like; and the like.

Preferable examples of the coating additive include light shielding agents such as titanium oxide and the like; glidants such as talc and the like; colorants such as red ferric oxide, yellow ferric oxide and the like; plasticizers such as polyethylene glycol (e.g., macrogol 6000), triethyl citrate, castor oil, polysorbates and the like; organic acids such as citric acid, tartaric acid, malic acid, ascorbic acid and the like; and the like.

The above-mentioned additive may be a mixture of two or more kinds at an appropriate ratio.

Granule (A) is preferably a composition composed of compound (A) or a salt thereof, an excipient (preferably mannitol), a disintegrant (preferably corn starch), and a binder (preferably hydroxypropylmethylcellulose) and, where necessary, a stabilizer (preferably succinic acid).

Examples of the dosage form of solid preparation (A) include oral preparations such as tablets (including sublingual tablet, orally disintegrating tablet), capsules (including soft capsule, microcapsule), powder, granule, troche and the like; and parenteral agents such as external preparations (e.g., dermal preparation, ointment), suppositories (e.g., rectal suppository, vaginal suppository), pellets and the like. These preparations may be release control preparations (e.g., sustained-release microcapsule) such as immediate-release preparation, sustained-release preparation and the like.

The shape of solid preparation (A) may be any such as round, caplet, oblong and the like.

Solid preparation (A) can be produced by formulating granule (A) and, where necessary, further additives into a preparation according to a method conventionally used in the technical field of pharmaceutical preparation.

Here, the further additives may be those similar to the aforementioned additives. The further additives may contain microcrystalline cellulose for the purpose of improving the formability of a solid preparation, increasing the hardness of a solid preparation and the like.

Microcrystalline cellulose is not particularly limited as long as it is used as an additive for a pharmaceutical product and, for example, one kind from microcrystalline cellulose [e.g., CEOLUS (grade: KG-802) (trade name); Avicel (grade: PH-302) (trade name]; Asahi Kasei Chemicals Corporation], microcrystalline cellulose (granules), microcrystalline cellulose (fine particles) and the like may be used alone, or two or more kinds thereof may be used as a mixture.

The above-mentioned further additives may be a mixture of two or more kinds at an appropriate ratio.

Solid preparation (A) can be produced by appropriately combining operations such as granulation, mixing, capsule filling, compression molding, coating and the like.

For granulation, for example, a granulation machine such as a high-shear granulator, a fluid bedgranulator and the like is used. For mixing, for example, a mixer such as a V-type mixer, a tumbler mixer and the like is used.

Compression molding includes punching using, for example, a single punch tableting machine, a rotary tableting machine and the like, at a pressure of generally 0.3-35 $kN/cm^2$. For coating, for example, a film coating apparatus is used. Here, as the coating base, for example, sugar coating base, aqueous film coating base, enteric film coating base, sustained-release film coating base and the like are used.

As the sugar coating base, aqueous film coating base, enteric film coating base, sustained-release film coating base and coating additive, those described as additives for granule (A) can be mentioned.

The above-mentioned coating base may be a mixture of two or more kinds at an appropriate ratio. In addition, a coating additive may be used during coating.

Moreover, solid preparation (A) may be stamped or printed with marks or letters for discrimination, or have a score line for dividing the tablet.

Specific examples of solid preparation (A) include
1) a mixed powder obtained by mixing granule (A) with, where necessary, the above-mentioned further additives;
2) a capsule obtained by mixing granule (A) with, where necessary, the above-mentioned further additives and filling a capsule (e.g., gelatin capsule) therewith;
3) a formed product (e.g., tablet) obtained by mixing granule (A) with, where necessary, the above-mentioned further additives and compression molding;
and the like.

Solid preparation (A) generally contains granule (A) of the present invention in a proportion of preferably 75-100 wt %, more preferably 75-95 wt %, more preferably 80-90 wt %.

In a preferable embodiment, solid preparation (A) is a tablet (sometimes to be abbreviated as "tablet (A)" in the is present specification).

In this embodiment, tablet (A) contains, besides granule (A), a tableting aid (sometimes to be abbreviated as "tableting aid (A)" in the present specification).

In the present specification, the "tableting aid" means a component to be mixed with the granule comprising compound (A) or a salt thereof before the tableting step during the production of the tablet. The component may contain one or more kinds of the below-mentioned additives.

Tableting aid (A) contains an additive conventionally used in the field of pharmaceutical preparations. As the additive, for example, the aforementioned further additives and the like can be recited. Unless otherwise specified, these additives are used in an amount conventionally used in the field of pharmaceutical preparations. In addition, tableting aid (A) may contain two or more kinds of these additives at an appropriate ratio.

Tableting aid (A) is preferably a composition composed of a lubricant (preferably magnesium stearate), microcrystalline cellulose (the microcrystalline cellulose may be substituted by one or more disintegrants selected from low-substituted hydroxypropylcellulose (L-HPC), carmellose calcium (calcium carboxymethylcellulose (CMC-Ca)) and the like), and a disintegrant (preferably croscarmellose sodium).

The content of the lubricant contained in tableting aid (A) in tablet (A) of the present invention is preferably 0.5-2 wt %, more preferably 0.5-1.5 wt %.

The content of the microcrystalline cellulose (or one or more disintegrants selected from low-substituted hydroxypropylcellulose (L-HPC), carmellose calcium and the like: a substitute for microcrystalline cellulose) contained in tableting aid (A) in tablet (A) of the present invention is preferably 2-20 wt %, more preferably 2-15 wt %.

The content of the disintegrant contained in tableting aid (A) in tablet (A) of the present invention is preferably 1-15 wt %, more preferably 1-10 wt %.

Tablet (A) of the present invention generally contains granule (A) of the present invention in an amount corresponding to the content of preferably 75-95 wt %, more preferably 80-90 wt %, and tableting aid (A) in an amount corresponding to the content of preferably 5-25 wt %, more preferably 10-20 wt %.

Preferable specific examples of the tablet (A) of the present invention include the following.

A tablet containing the following (a) and (b):
(a) granule (A) composed of compound (A) or a salt thereof (preferably succinate); an excipient other than microcrystalline cellulose (preferably mannitol), disintegrant (preferably corn starch) and a binder (preferably hydroxypropylmethylcellulose); and a stabilizer (preferably succinic acid) as necessary,
(b) tableting aid (A) composed of a lubricant (preferably magnesium stearate), microcrystalline cellulose (the microcrystalline cellulose may be substituted by one or more disintegrants selected from low-substituted hydroxypropylcellulose (L-HPC), carmellose calcium and the like), and a disintegrant (preferably croscarmellose sodium).

Tablet (A) of the present invention may be film-coated with the object of improvement of easy administrability, preparation strength and the like.

Preferable examples of the coating base and coating additive used for film coating include those similar to the ones used for the aforementioned granule (A).

When the tablet (A) is film-coated, the film coating layer can be formed in a proportion of generally 1-10 parts by weight, preferably 2-6 parts by weight, per 100 parts by weight of said tablet.

The tablet (A) of the present invention can be produced by mixing granule (A) and tableting aid (A), and punching the mixture.

As a preferable specific example, tablet (A) can be produced according to the following production steps. Each starting material used in the following production step is used in such amount as to achieve the aforementioned content per finally obtained tablet.

1) Granule (A) can be produced, for example, by mixing compound (A) or a salt thereof and an additive (excluding microcrystalline cellulose; e.g., excipient, disintegrant, as necessary, stabilizer), and granulating the mixture. More specifically, granulation is performed while spraying a dispersion liquid of a binder in a solvent (e.g., water, acetone, ethyl alcohol, propyl alcohol, and mixture thereof at appropriate ratio; preferably water) in a fluid bed granulator. Then, the product is dried, and the obtained granulates are milled to give milled granules.
2) Tableting aid (A) (e.g., lubricant, microcrystalline cellulose (or one or more disintegrants selected from low-substituted hydroxypropylcellulose (L-HPC), carmellose calcium and the like: a substitute for microcrystalline cellulose), and disintegrant) are added to and mixed with the milled granules to give tableting granules.
3) The granules are punched by a tableting machine to give a plain tablet.
4) When desired, a film coating solution is, for example, sprayed on the obtained plain tablet in a film coating machine to give film-coated tablets.

The above-mentioned dispersion liquid may be any of solution and suspension, and the "dispersion liquid" in the present specification includes both solution and suspension.

For the purpose of improving easy administrability, preparation strength and the like, tablet (A) of the present invention is preferably film-coated. In addition, said tablet (A) may be filled in a capsule (e.g., gelatin capsule) to give a capsule.

The tablet (A) of the present invention may be stamped or printed with marks or letters for discrimination, or have a score line for dividing the tablet.

The operations such as mixing, tableting, coating and the like in the above-mentioned production step are performed according to the aforementioned methods conventionally used in the technical field of pharmaceutical preparations.

In another aspect, the present invention relates to a tablet containing
(a) a granule containing compound (A) or a salt thereof and microcrystalline cellulose; and
(b) a tableting aid containing magnesium stearate and microcrystalline cellulose
(sometimes to be abbreviated as "tablet (B)" in the present specification).

Since tablet (B) of the present invention contains microcrystalline cellulose in both the granule part containing compound (A) or a salt thereof and the tableting aid, it can suppress tableting trouble caused by the properties of compound (A). As a result, a tablet superior in the formability, dissolution property of compound (A) and the like can be provided.

As mentioned above, in general, the size and weight of a solid preparation (including tablet) are limited to facilitate handling and administration. When the content of compound (A) in the preparation is increased, the increased amount needs to be compensated for by decreasing the content of various additives. In other words, when the content of compound (A) in the preparation increases, the content of additives decreases inversely. As a result, the level of tableting trouble caused by compound (A) increases. When a solid preparation having a high content of compound (A) in the preparation (e.g., as compound (A) (i.e., as free form), more than 25 wt %) is to be produced, therefore, use of tablet (B) capable of suppressing tableting trouble due to compound (A) is advantageous.

Tablet (B) of the present invention is explained in the following.

Component (a) in tablet (B) is a granule containing compound (A) or a salt thereof and microcrystalline cellulose (hereinafter sometimes to be abbreviated as "granule (B)").

The content of compound (A) or a salt thereof contained in tablet (B) of the present invention is generally 0.1-50 wt %, preferably more than 25 wt % to not more than 40 wt % as compound (A) (free form).

The microcrystalline cellulose to be used for granule (B) is not particularly limited as long as it is used as an additive for pharmaceutical products, and those recited as examples of the aforementioned further excipient can be mentioned.

The content of the microcrystalline cellulose contained in granule (B) in tablet (B) of the present invention is preferably 5-40 wt %, more preferably 5-20 wt %.

Granule (B) may further contain, besides microcrystalline cellulose, additives conventionally used in the field of pharmaceutical preparations. As the additive, those recited as examples of additive for the aforementioned granule (A) can be mentioned. The additives may be a mixture of two or more kinds at an appropriate ratio. Unless otherwise specified, the additives are used in an amount conventionally used in the field of pharmaceutical preparations.

Mannitol, an excipient, generally induces tableting trouble easily. In tablet (B) of the present invention, however, tableting trouble induced by mannitol can also prevented. Thus, addition of mannitol as an excipient to granule (B) of the present invention for the purpose of improving the water solubility, storage stability and the like of compound (A) (or a salt thereof), which is a pharmaceutically active ingredient, is preferable.

The content of the excipient contained in granule (B) in tablet (B) of the present invention is preferably 10-99.9 wt %, more preferably 10-35 wt %.

As the binder for granule (B), hydroxypropylmethylcellulose is preferable.

The content of the binder contained in granule (B) in tablet (B) of the present invention is preferably 1-30 wt %, more preferably 2-20 wt %.

For the purpose of improving the stability of compound (A), addition of the aforementioned stabilizer to granule (B) is preferable.

As the stabilizer for granule (B), succinic acid is preferable.

The content of the stabilizer contained in granule (B) in tablet (B) of the present invention is preferably 1-35 wt %, more preferably 1-10 wt %.

Granule (B) is preferably a composition composed of compound (A) or a salt thereof and microcrystalline cellulose, an excipient (preferably mannitol), a binder (preferably hydroxypropylmethylcellulose) and, where necessary, a stabilizer (preferably succinic acid).

Component (b) in tablet (B) is a tableting aid containing magnesium stearate and microcrystalline cellulose (hereinafter sometimes to be abbreviated as "tableting aid (B)").

Magnesium stearate to be used for tableting aid (B) is not particularly limited as long as it is used as an additive for pharmaceutical products.

The content of the magnesium stearate in tableting aid (B) in tablet (B) of the present invention is preferably 0.5-2 wt %, more preferably 0.5-1.5 wt %.

As microcrystalline cellulose to be used for tableting aid (B), those similar to one used for the aforementioned granule (B) can be mentioned. Here, the kind of microcrystalline cellulose to be used for the granule (B) and that to be used for the tableting aid may be the same or different.

The content of the microcrystalline cellulose contained in tableting aid (B) in tablet (B) of the present invention is preferably 2-20 wt %, more preferably 2-15 wt %.

Tableting aid (B) may further contain, besides magnesium stearate and microcrystalline cellulose, additives conventionally used in the field of pharmaceutical preparations. As the additive, those recited as examples of additive for the aforementioned granule (A) can be mentioned. The additives may be a mixture of two or more kinds at an appropriate ratio. Unless otherwise specified, the additives are used in an amount conventionally used in the field of pharmaceutical preparations.

Tableting aid (B) is a composition composed of, besides magnesium stearate and microcrystalline cellulose, preferably a disintegrant (preferably croscarmellose sodium or low-substituted hydroxypropylcellulose).

The content of the disintegrant contained in tableting aid (B) in tablet (B) of the present invention is preferably 1-15 wt %, more preferably 1-10 wt %.

Tablet (B) of the present invention generally contains granule (B) of the present invention preferably in a proportion of 75-95 wt %, more preferably 80-90 wt %, and tableting aid (B) of the present invention preferably in a proportion of 5-25 wt %, more preferably 10-20 wt %.

Tablet (B) of the present invention generally contains microcrystalline cellulose in granule (B) of the present invention preferably in a proportion of 5-40 wt %, more preferably 5-20 wt %, and microcrystalline cellulose in tableting aid (B) of the present invention preferably in a proportion of 2-20 wt %, more preferably 2-15 wt %.

Moreover, tablet (B) of the present invention generally contains magnesium stearate in tableting aid (B) of the present invention preferably in a proportion of 0.5-2 wt %, more preferably 0.5-1.5 wt %.

Preferable examples of tablet (B) include the following.

A tablet containing the following (a) and (b):
(a) granule (B) composed of compound (A) or a salt thereof (preferably succinate), microcrystalline cellulose, an excipient (preferably mannitol), a binder (preferably hydroxypropylmethylcellulose) and, where necessary, a stabilizer (preferably succinic acid); and
(b) tableting aid (B) composed of magnesium stearate, microcrystalline cellulose, a disintegrant (preferably croscarmellose sodium or low-substituted hydroxypropylcellulose).

Tablet (B) of the present invention may be film-coated for the purpose of improving easy administrability, preparation strength and the like. Tablet (B) can be coated in the same manner as in the film coating of the aforementioned tablet (A).

When tablet (B) is film-coated, the film coating layer can be formed in a proportion of generally 1-10 parts by weight, preferably 2-6 parts by weight, per 100 parts by weight of the tablet.

Tablet (B) of the present invention can be produced by mixing granule (B) and tableting aid (B), and punching the mixture.

Specifically, tablet (B) can be produced according to the following production steps. Each starting material used in the following production steps is used in such amount as to achieve the aforementioned content per finally obtained tablet.

1) Granule (B) can be produced, for example, by mixing compound (A) or a salt thereof and microcrystalline cellulose, and an additive (e.g., excipient, as necessary, stabilizer) as necessary, and granulating the mixture. More specifically, granulation is performed while spraying a dispersion liquid of a binder in a solvent (e.g., water, acetone, ethyl alcohol, propyl alcohol, and mixture thereof at appropriate ratio; preferably water) in a fluid bed granulator. Then, the product is dried, and the obtained granulates are milled to give milled granules.
2) Magnesium stearate and microcrystalline cellulose and, where necessary, an additive (e.g., disintegrant) as tableting aid (B) are added to and mixed with the milled granules to give granules for tableting.
3) The granules are punched by a tableting machine to give plain tablets.
4) When desired, a film coating solution is, for example, sprayed on the obtained plain tablet in a film coating machine to give film-coated tablets.

The above-mentioned dispersion liquid may be any of solution and suspension.

For the purpose of improving easy administrability, preparation strength and the like, tablet (B) of the present invention is preferably film-coated. In addition, said tablet (B) may be filled in a capsule (e.g., gelatin capsule) to give a capsule.

Tablet (B) of the present invention may be stamped or printed with marks or letters for discrimination, or have a score line for dividing the tablet.

The operations such as mixing, tableting, coating and the like in the above-mentioned production step are performed according to a conventionally used method in the technical field of preparation, as described for solid preparation (A).

The preparation of the present invention can be safely administered orally or parenterally to a mammal (e.g., mouse, rat, rabbit, cat, dog, bovine, horse, monkey, human).

The preparation of the present invention is useful for the prophylaxis or treatment of, for example, diabetes [e.g., type 1 diabetes, type 2 diabetes, type 1.5 diabetes (LADA (Latent Autoimmune Diabetes in Adults)), gestational diabetes, diabetes with impaired insulin secretion, obese diabetes, IGT (impaired glucose tolerance), IFG (Impaired Fasting Glucose), IFG (Impaired Fasting Glycaemia)], diabetic complications [e.g., neuropathy, nephropathy, retinopathy, cataract, macroangiopathy, arteriosclerosis, osteopenia, hyperosmolar diabetic coma, infections (e.g., respiratory infection, urinary tract infection, gastrointestinal infection, dermal soft tissue infection, inferior limb infection), diabetic gangrene, xerostomia, hypacusis, cerebrovascular disorder, peripheral blood circulation disorder], obesity, hyperlipidemia (e.g., hypertriglyceridemia, hypercholesterolemia, hypoHDL-emia, postprandial hyperlipemia), arteriosclerosis (e.g., atherosclerosis), hypertension, myocardial infarction, angina pectoris, cerebrovascular disorder (e.g., cerebral infarction, cerebral apoplexy), insulin resistance syndrome, syndrome X, dysmetabolic syndrome and the like.

In addition, the preparation of the present invention is also useful for secondary prevention of the above-mentioned various diseases (e.g., secondary prevention of cardiovascular event such as myocardial infarction and the like) or suppression of progression [e.g., suppression of progression from impaired glucose tolerance to diabetes; suppression of progression from diabetes to diabetic complications (preferably diabetic neuropathy, diabetic nephropathy, diabetic retinopathy, arteriosclerosis)].

The dose of the preparation of the present invention only needs to contain an effective amount of compound (A) as a pharmaceutically active ingredient.

As a specific example, an effective amount of compound (A) or a salt thereof for administration at intervals of 24 hr or less (e.g., 1-3 times a day) is, based on compound (A) (free form), generally 1 mg-50 mg, preferably 1 mg-25 mg, per administration to one adult (body weight 60 kg) and, for administration at intervals of longer than one day (e.g., once in 3 days -1 week) is generally 1 mg-500 mg, preferably 1 mg-400 mg, more preferably 1 mg-250 mg, still more preferably 25 mg-200 mg, per administration.

Granule (A), solid preparation (A), and tablet (A) of the present invention are preferable for the administration at the above-mentioned 24 hr intervals or less from the aspect of the stability of compound (A) or a salt thereof. Tablet (B) of the present invention is preferable for the administration at the above-mentioned intervals exceeding one day, from the aspect of the tablet formability and dissolution property of compound (A).

Particularly preferable examples of tablet (A) of the present invention include
"a tablet containing 3.125 mg of compound (A) (free form) per tablet";
"a tablet containing 12.5 mg of compound (A) (free form) per tablet"; and
"a tablet containing 25 mg of compound (A) (free form) per tablet".

Particularly preferable examples of tablet (B) of the present invention include
"a tablet containing 50 mg of compound (A) (free form) per tablet";
"a tablet containing 100 mg of compound (A) (free form) per tablet"; and
"a tablet containing 200 mg of compound (A) (free form) per tablet".

Compound (A) or a salt thereof can be used in combination with one or more other kinds of different pharmaceutical agents (hereinafter sometimes to be abbreviated as "concomitant drug").

Specific examples thereof include a combined use of compound (A) or a salt thereof and one or more pharmaceutical agents (concomitant drug) selected from a therapeutic agent for diabetes, a therapeutic agent for diabetic complications, a therapeutic agent for hyperlipidemia, an antihypertensive agent, an antiobestic agent, a diuretic, an antithrombotic agent and the like.

Examples of the therapeutic agent for diabetes include insulin preparations (e.g., animal insulin preparation extracted from the pancreas of bovine, swine; human insulin preparation synthesized by genetic engineering using *Escherichia coli* or yeast; zinc insulin; protamine zinc insulin; fragment or derivative of insulin (e.g., INS-1), oral insulin preparation), insulin sensitizers (e.g., pioglitazone or a salt thereof (preferably hydrochloride), rosiglitazone or a salt thereof (preferably maleate), tesaglitazar, ragaglitazar, muraglitazar, edaglitazone, metaglidasen, naveglitazar, AMG-131, THR-0921), α-glucosidase inhibitors (e.g., voglibose, acarbose, miglitol, emiglitate), biguanides (e.g., metformin, buformin or a salt thereof (e.g., hydrochloride, fumarate, succinate)), insulin secretagogue [sulfonylurea (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or a calcium salt hydrate thereof], dipeptidyl peptidase IV inhibitors other than compound (A) (e.g., alogliptin or a salt thereof (preferably benzoate), vildagliptin, sitagliptin, saxagliptin, T-6666, TS-021), β3 agonists (e.g., AJ-9677), GPR40 agonists, GLP-1 receptor agonists [e.g., GLP-1, GLP-1MR agent, NN-2211, AC-2993 (exendin-4), BIM-51077, Aib(8, 35)hGLP-1(7,37)NH$_2$, CJC-1131], amylin agonists (e.g., pramlintide), phosphotyrosine phosphatase inhibitors (e.g., sodium vanadate), gluconeogenesis inhibitors (e.g., glycogen phosphorylase inhibitor, glucose-6-phosphatase inhibitor, glucagon antagonist), SGLUT (sodium-glucose cotransporter) inhibitors (e.g., T-1095), 11β-hydroxysteroid dehydrogenase inhibitors (e.g., BVT-3498), adiponectin or agonist thereof, IKK inhibitors (e.g., AS-2868), leptin resistance improving drugs, somatostatin receptor agonists, glucokinase activators (e.g., Ro-28-1675), GIP (glucose-dependent insulinotropic peptide) and the like.

Examples of the therapeutic agents for diabetic complications include aldose reductase inhibitors (e.g., tolrestat, epalrestat, zenarestat, zopolrestat, minalrestat, fidarestat, CT-112), neurotrophic factors and increasing drugs thereof (e.g., NGF, NT-3, BDNF, neurotrophin production/secretion promoting agent described in WO01/14372 (e.g., 4-(4-chlorophenyl)-2-(2-methyl-1-imidazolyl)-5-[3-(2-methylphenoxy)propyl]oxazole)), nerve regeneration promoters (e.g., Y-128), PKC inhibitors (e.g., ruboxistaurin mesylate), AGE inhibitors (e.g., ALT946, pimagedine, N-phenacylthiazolium bromide (ALT766), ALT-711, EXO-226, Pyridorin, pyridoxamine), active oxygen scavengers (e.g., thioctic acid), cerebral vasodilators (e.g., tiapuride, mexiletine), somatostatin receptor agonists (e.g., BIM23190), and apoptosis signal regulating kinase-1 (ASK-1) inhibitors.

Examples of the therapeutic agent for hyperlipidemia include HMG-CoA reductase inhibitors (e.g., pravastatin, simvastatin, lovastatin, atorvastatin, fluvastatin, pitavastatin, rosuvastatin or salts thereof (e.g., sodium salt, calcium salt)), squalene synthase inhibitors (e.g., lapaquistat or a salt thereof (preferably acetate)), fibrate compounds (e.g., bezafibrate, clofibrate, simfibrate, clinofibrate), ACAT inhibitors (e.g., avasimibe, eflucimibe), anion exchange resins (e.g., colestyramine), probucol, nicotinic acid drugs (e.g., nicomol, niceritrol), ethyl icosapentate, phytosterol (e.g., soysterol, γ-oryzanol) and the like.

Examples of the antihypertensive agent include angiotensin converting enzyme inhibitors (e.g., captopril, enalapril, delapril), angiotensin II receptor antagonists (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid), calcium antagonists (e.g., manidipine, nifedipine, amlodipine, efonidipine, nicardipine), potassium channel openers (e.g., levcromakalim, L-27152, AL 0671, NIP-121), clonidine and the like.

Examples of the antiobestic agent include antiobestic agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds described in WO01/82925 and WO01/87834); neuropeptide Y antagonists (e.g., CP-422935); cannabinoid receptor antagonists (e.g., SR-141716, SR-147778); ghrelin antagonist), pancreatic lipase inhibitors (e.g., orlistat, cetilistat), β3 agonists (e.g., AJ-9677), anorectic peptides (e.g., leptin, CNTF (ciliary neurotrophic factor)), cholecystokinin agonists (e.g., lintitript, FPL-15849), feeding deterrents (e.g., P-57) and the like.

Examples of the diuretic include xanthine derivatives (e.g., theobromine sodium salicylate, theobromine calcium salicylate), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide), antialdosterone preparations (e.g., spironolactone, triamterene), carbonic anhydrase inhibitors (e.g., acetazolamide), chlorobenzenesulfonamide agents (e.g., chlortalidone, mefruside, indapamide), azosemide, isosorbide, ethacrynic acid, piretanide, bumetanide, furosemide and the like.

Examples of the antithrombotic agent include heparins (e.g., heparin sodium, heparin calcium, dalteparin sodium), warfarins (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium, sarpogrelate hydrochloride) and the like.

Of the above-mentioned concomitant drugs, insulin sensitizers (preferably pioglitazone hydrochloride), insulin preparation, α-glucosidase inhibitors (preferably voglibose, acarbose), biguanides (preferably metformin hydrochloride), sulfonylureas (preferably glimepiride) and the like are preferable.

When the preparation of the present invention and a concomitant drug are used in combination, the administration time of these is not limited, and they may be administered simultaneously to a subject of administration, or may be administered with a time difference.

In addition, the preparation of the present invention and the concomitant drug may be administered as separate preparations to an administration subject, or they may be administered to an administration subject as a single preparation containing the preparation of the present invention and the concomitant drug.

The dose of the concomitant drug can be appropriately determined based on the clinically employed dose of each drug. In addition, the mixing ratio of the preparation of the present invention and the concomitant drug can be appropriately determined according to the administration subject, administration route, target disease, condition, combination and the like. For example, when the administration subject is a human, the concomitant drug may be used in an amount of 0.01 to 100 parts by weight per 1 part by weight of the preparation of the present invention.

Use of the combination drug in this way provides superior effects such as 1) enhanced effect of the action of compound (A) (or a salt thereof) or a concomitant drug (synergistic effect of pharmaceutical agent actions), 2) reduction effect of the dose of compound (A) (or a salt thereof) or a concomitant drug (reduction effect of pharmaceutical agent dose as compared to single drug administration), 3) reduction effect of secondary action of compound (A) (or a salt thereof) or a concomitant drug, and the like.

The present invention is explained in more detail in the following by referring to Comparative Example, Example and Experimental Examples, which are not to be construed as limitative.

As additives for pharmaceutical preparations in the following Comparative Examples and Examples, the Japanese Pharmacopoeia 15th edition, the Japanese Pharmaceutical Codex or Japanese Pharmaceutical Excipients 2003 compatible products were used.

EXAMPLES

Comparative Example 1A

Succinate of compound (A) (26.6 mg) was weighed in a glass bottle and used as Comparative Example 1A.

Comparative Example 2A

The succinate of compound (A) and microcrystalline cellulose were uniformly mixed in a mortar at a ratio of 1:10, and the mixture (226.6 mg) was weighed in a glass bottle and used as Comparative Example 2A.

Comparative Example 3A

The succinate of compound (A) and corn starch were uniformly mixed in a mortar at a ratio of 1:5, and the mixture (126.6 mg) was weighed in a glass bottle and used as Comparative Example 3A.

Example 1A

Succinate of compound (A), mannitol and corn starch according to the formulation of Table 1A were uniformly mixed in a fluid bed granulator (LAB-1, POWREX CORPORATION), and the mixture was granulated by spraying an aqueous solution of dissolved hypromellose 2910, and dried therein. The obtained granules were passed through a sieve (16M) to give milled granules. To the milled granules were added croscarmellose sodium, microcrystalline cellulose and magnesium stearate, and they were mixed in a bag to give granules for tableting. The granules were punched by a rotary tableting machine (Correct 19K, Kikusui Seisakusho, Ltd.) with a 6.5 mmφ punch to give a plain tablet weighting 121 mg. On the other hand, titanium oxide, yellow ferric oxide and talc were dispersed in a hypromellose 2910 aqueous solution to prepare a film coating liquid. The aforementioned coating liquid was sprayed onto the above-mentioned plain tablet in a film coating machine (Hicoater HCP-75, Freund Corporation), to give 2500 film-coated tablets containing 3.125 mg of compound (A) (free form) per tablet.

TABLE 1A

| component | compound (A) free form 3.125 mg tablet mg/tablet |
|---|---|
| (granule) | |
| succinate of compound (A) | 4.156 |
| mannitol | 64.394 |
| corn starch | 29.35 |
| hypromellose 2910 | 5.5 |
| (tableting aid) | |
| croscarmellose sodium | 5.5 |
| microcrystalline cellulose | 11 |
| magnesium stearate | 1.1 |
| (film coating) | |
| hypromellose 2910 | 3.875 |
| titanium oxide | 0.5 |
| talc | 0.6 |
| yellow ferric oxide | 0.025 |
| weight | 126 |

Example 2A

A tablet having the formulation of Table 2A can be produced in the same manner as in Example 1A except that succinate of compound (A), mannitol, corn starch and succinic acid are first mixed uniformly.

TABLE 2A

| component | compound (A) free form 3.125 mg tablet mg/tablet |
|---|---|
| (granule) | |
| succinate of compound (A) | 4.156 |
| mannitol | 59.394 |
| corn starch | 29.35 |
| succinic acid | 5 |
| hypromellose 2910 | 5.5 |
| (tableting aid) | |
| croscarmellose sodium | 5.5 |
| microcrystalline cellulose | 11 |
| magnesium stearate | 1.1 |
| (film coating) | |
| hypromellose 2910 | 3.875 |
| titanium oxide | 0.5 |
| talc | 0.6 |
| yellow ferric oxide | 0.025 |
| weight | 126 |

Example 3A

A tablet having the formulation of Table 3A can be produced in the same manner as in Example 1A except that microcrystalline cellulose is changed to low-substituted hydroxypropylcellulose (L-HPC).

TABLE 3A

| component | compound (A) free form 3.125 mg tablet mg/tablet |
|---|---|
| (granule) | |
| succinate of compound (A) | 4.156 |
| mannitol | 64.394 |
| corn starch | 29.35 |
| hypromellose 2910 | 5.5 |
| (tableting aid) | |
| croscarmellose sodium | 5.5 |
| L-HPC | 11 |
| magnesium stearate | 1.1 |
| (film coating) | |
| hypromellose 2910 | 3.875 |
| titanium oxide | 0.5 |
| talc | 0.6 |
| yellow ferric oxide | 0.025 |
| weight | 126 |

Example 4A

A tablet having the formulation of Table 4A can be produced in the same manner as in Example 1A except that succinate of compound (A), mannitol, corn starch and succinic acid are first mixed uniformly and microcrystalline cellulose is changed to low-substituted hydroxypropylcellulose (L-HPC).

TABLE 4A

| component | compound (A) free form 3.125 mg tablet mg/tablet |
|---|---|
| (granule) | |
| succinate of compound (A) | 4.156 |
| mannitol | 59.394 |
| corn starch | 29.35 |
| succinic acid | 5 |
| hypromellose 2910 | 5.5 |
| (tableting aid) | |
| croscarmellose sodium | 5.5 |
| L-HPC | 11 |
| magnesium stearate | 1.1 |
| (film coating) | |
| hypromellose 2910 | 3.875 |
| titanium oxide | 0.5 |
| talc | 0.6 |
| yellow ferric oxide | 0.025 |
| weight | 126 |

Example 5A

Succinate of compound (A), mannitol and corn starch according to the formulation of Table 5A were uniformly mixed in a fluid bed granulator (FD-5S, POWREX CORPORATION), and the mixture was granulated by spraying an aqueous solution of dissolved hydroxypropylmethylcellulose (TC-5RW; Shin-Etsu Chemical Co., Ltd.), and dried therein. The obtained granules were milled by a particle sizing machine (Powermill P-3, Showa Chemical Machinery) to give milled granules. To the milled granules were added croscarmellose sodium, microcrystalline cellulose and magnesium stearate, and they were mixed in a mixing machine (Tumbler 15L; Showa Chemical Machinery) to give granules for tableting. The granules were punched by a rotary tableting machine (Correct 12HUK, Kikusui Seisakusho, Ltd.) with a 6.5 mmϕ punch to give a plain tablet weighting 121 mg. On the other hand, titanium oxide, yellow ferric oxide and talc were dispersed in a hydroxypropylmethylcellulose (TC-5RW; Shin-Etsu Chemical Co., Ltd.) aqueous solution to prepare a film coating liquid. The aforementioned coating liquid was sprayed onto the above-mentioned plain tablet in a film coating machine (Driacoater DCR500, Powrex Corporation), to give 26,000 film-coated tablets containing 12.5 mg of compound (A) (free form) per tablet.

TABLE 5A

| component | compound (A) free form 12.5 mg tablet mg/tablet |
|---|---|
| (granule) | |
| succinate of compound (A) | 16.625 |
| mannitol | 51.925 |
| corn starch | 29.35 |
| hydroxypropylmethylcellulose (TC-5RW) (tableting aid) | 5.5 |
| croscarmellose sodium | 5.5 |
| microcrystalline cellulose | 11 |
| magnesium stearate | 1.1 |
| (film coating) | |
| hydroxypropylmethylcellulose (TC-5RW) | 3.875 |
| titanium oxide | 0.5 |
| yellow ferric oxide | 0.025 |
| talc | 0.6 |
| weight | 126 |

Example 6A

Succinate of compound (A), mannitol and corn starch according to the formulation of Table 6A were uniformly mixed in a fluid bed granulator (FD-5S, POWREX CORPORATION), and the mixture was granulated by spraying an aqueous solution of dissolved hydroxypropylmethylcellulose (TC-5RW; Shin-Etsu Chemical Co., Ltd.), and dried therein. The obtained granules were milled by a particle sizing machine (Powermill P-3, Showa Chemical Machinery) to give milled granules. To the milled granules were added croscarmellose sodium, microcrystalline cellulose and magnesium stearate, and they were mixed in a mixing machine (Tumbler 15L; Showa Chemical Machinery) to give granules for tableting. The granules were punched by a rotary tableting machine (Correct 12HUK, Kikusui Seisakusho, Ltd.) with a 6.5 mmϕ punch to give a plain tablet weighting 121 mg. On the other hand, titanium oxide, yellow ferric oxide and talc were dispersed in a hydroxypropylmethylcellulose (TC-5RW; Shin-Etsu Chemical Co., Ltd.) aqueous solution to prepare a film coating liquid. The aforementioned coating liquid was sprayed onto the above-mentioned plain tablet in a film coating machine (Driacoater DCR500, Powrex Corporation), to give 26,000 film-coated tablets containing 25 mg of compound (A) (free form) per tablet.

TABLE 6A

| component | compound (A) free form 25 mg tablet mg/tablet |
|---|---|
| (granule) | |
| succinate of compound (A) | 33.25 |
| mannitol | 35.3 |
| corn starch | 29.35 |
| hydroxypropylmethyl cellulose (TC-5RW) (tableting aid) | 5.5 |
| croscarmellose sodium | 5.5 |
| microcrystalline cellulose | 11 |
| magnesium stearate | 1.1 |
| (film coating) | |
| hydroxypropylmethylcellulose (TC-5RW) | 3.875 |
| titanium oxide | 0.5 |
| yellow ferric oxide | 0.025 |
| talc | 0.6 |
| weight | 126 |

Comparative Example 1B

Succinate of compound (A), mannitol, microcrystalline cellulose according to the formulation of Table 1B were uniformly mixed in a fluid bed granulator (LAB-1, POWREX CORPORATION), and the mixture was granulated by spraying an aqueous solution of dissolved hypromellose 2910 and dried therein. The obtained granules were passed through a sieve (16M) to give milled granules. To the milled granules were added croscarmellose sodium and magnesium stearate, and they were mixed in a bag to give granules for tableting. The granules were punched by a rotary tableting machine (Correct 19K, Kikusui Seisakusho, Ltd.) with a 9.0 mmϕ punch to give a plain tablet weighting 300 mg. However, plain tablets could not be produced due to tableting trouble (sticking and capping).

TABLE 1B

| component | compound (A) free form 100 mg tablet mg/tablet |
|---|---|
| (granule) | |
| succinate of compound (A) | 133 |
| mannitol | 108.8 |
| microcrystalline cellulose | 25.2 |
| hypromellose 2910 (tableting aid) | 15 |
| croscarmellose sodium | 15 |
| magnesium stearate | 3 |
| weight | 300 |

Example 1B

Succinate of compound (A), mannitol and microcrystalline cellulose according to the formulation of Table 2B were uniformly mixed in a fluid bed granulator (LAB-1, POWREX CORPORATION), and the mixture was granulated by spraying an aqueous solution of dissolved hypromellose 2910, and dried therein. The obtained granules were passed through a sieve (16M) to give milled granules. To the milled granules were added croscarmellose sodium, microcrystalline cellulose and magnesium stearate, and they were mixed in a bag to give granules for tableting. The granules were punched by a rotary tableting machine (Correct 19K, Kikusui Seisakusho, Ltd.) with a 9.0 mmφ punch to give a plain tablet weighting 300 mg. On the other hand, titanium oxide, red ferric oxide, yellow ferric oxide and talc were dispersed in an aqueous solution of dissolved hypromellose 2910 and macrogol 6000 to prepare a film coating liquid. The aforementioned coating liquid was sprayed onto the above-mentioned plain tablet in a film coating machine (Hicoater HCP-75, Freund Corporation), to give 1000 film-coated tablets containing 100 mg of compound (A) (free form) per tablet. In the present Example, tableting trouble such as capping and sticking, and the like was not observed.

TABLE 2B

| component | compound (A) free form 100 mg tablet mg/tablet |
|---|---|
| (granule) | |
| succinate of compound (A) | 133 |
| mannitol | 93.8 |
| microcrystalline cellulose | 25.2 |
| hypromellose 2910 (tableting aid) | 15 |
| croscarmellose sodium | 15 |
| microcrystalline cellulose | 15 |
| magnesium stearate | 3 |
| (film coating) | |
| hypromellose 2910 | 6.9 |
| titanium oxide | 1.2 |
| macrogol 6000 | 1.8 |
| talc | 1.5 |
| red ferric oxide | 0.15 |
| yellow ferric oxide | 0.45 |
| weight | 312 |

Experimental Example 1A

Comparative Examples 1A, 2A and 3A were preserved in a glass bottle with an opened cap at 40° C., 75% RH for 2 weeks, and the amount of analogs due to decomposition of compound (A) was measured, based on which the storage stability was evaluated. The results are shown in the following Table 12A.

The amounts of the analogs were measured by high performance liquid chromatography (HPLC) under the conditions of Table 11A. As a result, an analogue that specifically increases at relative retention time (RRT) of about 1.65 was observed.

TABLE 11A

| mobile phase: | A: Water/ACN/TFA (1900:100:1) |
| | B: ACN/water/TFA (1900:100:1) |
| column: | Zorbax SB-CN, 5-μm, 4.6-mm i.d. × 25-cm, or equivalent, |
| column temperature: | 35° C. |
| sample concentration: | ~200 μg/mL |
| sample temperature: | 10° C. |
| injection volume; | 20 μL |
| measurement wavelength: | 278 nm |
| measurement time: | 60 min |
| flow rate: | 1 mL/min |
| gradient (linear): | Time (min)   MP-A (%)   MP-B (%) |

TABLE 11A-continued

| | | |
|---|---|---|
| 0 | 99 | 1 |
| 30 | 75 | 25 |
| 50 | 10 | 90 |
| 51 | 99 | 1 |
| 60 | 99 | 1 |

TABLE 12A

| | mixing ratio (compound (A)/additive) | initial total amount of analogs (%) | 40° C./75% RH 2 wk (with opened cap) total amount of analogs (%) |
|---|---|---|---|
| compound (A) | — | 0.30 | 0.30 |
| compound (A)/ microcrystalline cellulose | 1/10 | 0.28 | 0.34 |
| compound (A)/ corn starch | 1/5 | 0.59 | 0.60 |

The above results show that solid preparation (A) containing granule (A) free of microcrystalline cellulose of the present invention is superior in the stability of compound (A) or a salt thereof.

Experimental Example 2A

Tablets of Examples 5A and 6A were preserved in a glass bottle with an opened cap at 40° C., 75% RH for 1 month, and the amount of analogs due to decomposition of compound (A) was measured, based on which the storage stability was evaluated. The results are shown in the following Table 13A.

The amounts of the analogs were measured by high performance liquid chromatography (HPLC) under the same condition of Experimental Example 1A.

TABLE 13A

| | initial total amount of analogs (%) | 40° C./75% RH 1 M (with opened cap) total amount of analogs (%) |
|---|---|---|
| Example 5A | 0.62 | 0.65 |
| Example 6A | 0.64 | 0.66 |

The above results show that solid preparation (A) containing granule (A) free of microcrystalline cellulose of the present invention is superior in the stability of compound (A) or a salt thereof.

Experimental Example 1B

According to the Japanese Pharmacopoeia Paddle Method (rpm number: 50 rpm, 37° C., 0.01N HCl 900 mL, n=3), the dissolution behavior of compound (A) from the plain tablet (100 mg tablet; tableting pressure 10 kN) obtained in Example 1B was measured. The results of the drug dissolution rate in 15 min after the dissolution test are shown in Table 11B below.

TABLE 11B

| | average dissolution rate ± S.D. (%) |
|---|---|
| Example 1B | 87 ± 8.4 |

The above results show that tablet (B) of the present invention can be produced without a tableting trouble, and is superior in the dissolution property of the pharmaceutically active ingredient.

INDUSTRIAL APPLICABILITY

The present invention can advantageously provide a solid preparation superior in the formability, and dissolution property and storage stability of compound (A), and the like.

This application is based on application No. 2007-064245 filed in Japan, the contents of which are incorporated hereinto by reference.

The invention claimed is:

1. A tablet comprising a granule composed of 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof and an additive, wherein the additive does not comprise microcrystalline cellulose, wherein said 2-[[6-[(3R)-3R)-3-amino-1-piperidinyl]-3,4-dihydro-3-methyl-2,4-dioxo-1(2H)-pyrimidinyl]methyl]-4-fluorobenzonitrile is contained in a proportion of 1 to 25 wt % relative to the tablet.

2. The tablet of claim 1, further comprising a tableting aid comprising magnesium stearate and microcrystalline cellulose.

3. The tablet of claim 2, wherein the content of the microcrystalline cellulose is 2 to 20 wt %.

4. A tablet comprising the following (a) and (b):
(a) a granule comprising 2-[[6-[(3R)-3-amino-1-piperidinyl]3,4-dihydro-3-methyl-2,4-dioxo-1(2H)-pyrimidinyl]methyl]-4-fluorobenzonitrile or a salt thereof and microcrystalline cellulose; and
(b) a tableting aid comprising magnesium stearate and microcrystalline cellulose, wherein said 2-[[6-[(3R)-3-amino-1-piperidinyl]-3,4-dihydro-3-methyl-2,4-dioxo-1(2H)-pyrimidinyl]methyl]-4-fluorobenzonitrile is contained in a proportion of more than 25 wt % to no more than 40 wt % relative to the tablet.

5. The tablet of claim 4, wherein the content of the microcrystalline cellulose of (a) is 5-40 wt % and the content of the microcrystalline cellulose of (b) is 2-20 wt %, both relative to the tablet.

6. A method of producing a tablet, which comprises mixing (a) a granule comprising 2-[[6-[(3R)-3-amino-1-piperidinyl]-3,4-dihydro-3-methyl-2,4-dioxo-1(2H)-pyrimidinyl]methyl]-4-fluorobenzonitrile or a salt thereof and microcrystalline cellulose, and (b) a tableting aid comprising magnesium stearate and microcrystalline cellulose, and then punching the mixture, wherein said 2-[[6-[(3R)-3-amino-1-piperidinyl]-3,4-dihydro-3-methyl-2,4-dioxo-1(2H)-pyrimidinyl]methyl]-4-fluorobenzonitrile is contained in a proportion of more than 25 wt % to not more than 40 wt % relative to the tablet.

7. The production method of claim 6, wherein the content of the microcrystalline cellulose of (a) is 5-40 wt % and the content of the microcrystalline cellulose of (b) is 2-20 wt %, both relative to the tablet.

* * * * *

UNITED STATES PATENT AND TRADEMARK OFFICE
CERTIFICATE OF CORRECTION

PATENT NO.         : 7,994,183 B2                                    Page 1 of 1
APPLICATION NO.    : 12/450118
DATED              : August 9, 2011
INVENTOR(S)        : Yusuke Murakawa and Miyuki Hohokabe It is certified that error appears in the above-identified patent and that said Letters Patent is hereby corrected as shown below:

Col. 21, claim 1, line 20, "3R)-3-amino-1-piperidinyl" should be --3-amino-1-piperidinyl--.

Signed and Sealed this
Fourteenth Day of February, 2012

David J. Kappos
*Director of the United States Patent and Trademark Office*